United States Patent
Dutheil-Gouret et al.

(10) Patent No.: US 9,005,593 B2
(45) Date of Patent: Apr. 14, 2015

(54) METHOD FOR SHAPING THE HAIR USING AT LEAST ONE REDUCING COMPOSITION, AT LEAST ONE CARE COMPOSITION, AND HEATING

(75) Inventors: Katia Dutheil-Gouret, Plaisir (FR); Marion Pallanchard, Montrouge (FR); Aude Livoreil, Paris (FR)

(73) Assignee: L'Oreal, Paris (FR)

( * ) Notice: Subject to any disclaimer, the term of this patent is extended or adjusted under 35 U.S.C. 154(b) by 543 days.

(21) Appl. No.: 12/760,769

(22) Filed: Apr. 15, 2010

(65) Prior Publication Data

US 2010/0263683 A1   Oct. 21, 2010

Related U.S. Application Data

(60) Provisional application No. 61/176,585, filed on May 8, 2009.

(30) Foreign Application Priority Data

Apr. 15, 2009 (FR) ...................................... 09 52475

(51) Int. Cl.
| | | |
|---|---|---|
| A61Q 5/04 | (2006.01) | |
| A61K 8/73 | (2006.01) | |
| A61K 8/81 | (2006.01) | |
| A61K 8/84 | (2006.01) | |
| A61K 8/88 | (2006.01) | |
| A61K 8/898 | (2006.01) | |

(52) U.S. Cl.
CPC ............... *A61K 8/731* (2013.01); *A61K 8/8158* (2013.01); *A61K 8/8182* (2013.01); *A61K 8/84* (2013.01); *A61K 8/88* (2013.01); *A61K 8/898* (2013.01); *A61Q 5/04* (2013.01)

(58) Field of Classification Search
None
See application file for complete search history.

(56) References Cited

U.S. PATENT DOCUMENTS

| | | | |
|---|---|---|---|
| 5,637,295 A * | 6/1997 | Lang et al. ................... 424/70.2 |
| 5,932,201 A * | 8/1999 | de Labbey et al. ......... 424/70.17 |
| 6,916,467 B2 | 7/2005 | Devin-Baudoin et al. |
| 7,128,902 B2 | 10/2006 | Legrand et al. |
| 7,393,365 B2 * | 7/2008 | Bureiko et al. ................... 8/101 |
| 7,754,193 B2 * | 7/2010 | Fondin et al. ................ 424/70.2 |
| 2001/0023235 A1 * | 9/2001 | Crudele et al. ................ 510/122 |
| 2002/0176875 A9 * | 11/2002 | Douin et al. ................... 424/401 |
| 2003/0115685 A1 | 6/2003 | Devin-Baudoin et al. |
| 2005/0112076 A1 | 5/2005 | Fondin et al. |
| 2005/0238599 A1 | 10/2005 | Devin-Baudoin et al. |
| 2008/0274070 A1 | 11/2008 | Campain et al. |
| 2009/0004130 A1 | 1/2009 | Wood et al. |
| 2009/0074699 A1 | 3/2009 | Biganska et al. |

FOREIGN PATENT DOCUMENTS

| | | | |
|---|---|---|---|
| EP | 0 723 772 A1 | 7/1996 | |
| EP | 1 312 351 A1 | 5/2003 | |
| EP | 1 312 650 A2 | 5/2003 | |
| EP | 1 486 196 A1 | 12/2004 | |
| EP | 1 880 706 A1 | 1/2008 | |
| EP | 1 935 396 A1 | 6/2008 | |
| EP | 1 944 011 A1 | 7/2008 | |
| EP | 2 011 478 A1 | 1/2009 | |
| EP | 2 039 343 A1 | 3/2009 | |
| FR | 2855045 | * 11/2004 | |

OTHER PUBLICATIONS

French Search Report for FR 0952475, dated Jan. 7, 2010.
English language abstract of EP 1 944 011 A1, Jul. 16, 2008.
English language translation of Japanese Office Action for JP 2010-093067, mailed May 19, 2014, (5 pages).
English language abstract for EP 1944011 (Jul. 16, 2008).

* cited by examiner

*Primary Examiner* — Jyothsna Venkat
(74) *Attorney, Agent, or Firm* — The Marbury Law Group, PLLC

(57) ABSTRACT

The present disclosure relates to a method for shaping hair fibers comprising: applying to the hair fibers at least one reducing composition comprising at least one reducing agent and at least one cationic polymer, wherein the weight ratio of the at least one reducing agent to the at least one cationic polymer ranges from 0.1:1 to 10:1; rinsing the hair fibers; applying at least one care composition comprising at least one aminated silicone; optionally rinsing the hair fibers; and heating the hair fibers with a heating device at a temperature ranging from 50 to 280° C., the heating being carried out before or after an optional rinsing of the hair fibers.

14 Claims, No Drawings

METHOD FOR SHAPING THE HAIR USING AT LEAST ONE REDUCING COMPOSITION, AT LEAST ONE CARE COMPOSITION, AND HEATING

This application claims benefit of U.S. Provisional Application No. 61/176,585, filed May 8, 2009. This application also claims benefit of priority under 35 U.S.C. §119 to French Patent Application No. 0952475, filed Apr. 15, 2009.

The present disclosure relates to a method for treating hair fibers.

It is known, in order to obtain permanent deformation of the hair, to carry out, in a first step, the opening of the disulphide bonds of the keratin (cystine) using a composition comprising a reducing agent and then, for example after having rinsed the hair, in reconstituting, in a second step, the said disulphide bonds by applying, to the hair which has been smoothed or placed beforehand under tension by appropriate devices, such as curlers, an oxidizing composition, also known as fixative, so as to give the desired shape to the hair. This technique can make it possible without distinction either to wave the hair or to straighten, crimp, or smooth it.

The reducing compositions which can be used for the implementation of the first stage of these methods generally comprise thiol-comprising compounds, such as thioglycolic acid, cysteine, cysteamine, thiolactic acid, and glycerol monothioglycolate.

The concentration of reducing agents can be very high, often up to 15% by weight of the reducing composition.

Such a technique may not be entirely satisfactory. This is because this technique may be very effective in modifying the shape of the hair but also very damaging to the hair fibers.

In addition, it has been discussed in the art to raise the temperature of the hair, between the reduction stage and the fixing stage, using a heating iron.

For example, Patent Application EP1 584 329 discloses a process for the treatment of hair fibers without fixing comprising the following stages:

applying to the hair fibers a ceramide-free reducing composition comprising at least one reducing agent, the at least one reducing agent being chosen from thiols and representing less than 3% by weight of the total weight of the reducing composition, if the composition does not comprise any aminothiol compound, and less than 5%, if the composition comprises at least one aminothiol compound, and raising the temperature of the hair fibers, using a heating iron, at a temperature of at least 60° C., the raising of the temperature being carried out before or after the optional rinsing of the hair fibers.

However, such a technique may result in inadequate shaping and in problems of residual odors and requires meticulous application of the iron.

The present disclosure thus provides a method for the treatment of hair fibers which may overcome at least one of the disadvantages of the prior art.

For example, the disclosed method for the treatment of hair fibers can make it possible to modify the shape of the hair, to control the volume of the hair, to reduce frizziness and to improve the cosmetic performance of the hair, such as the softness, the sheen, and the disentangling, while showing better retention of the color of dyed hair.

The disclosed method can also facilitate subsequent blow drying or smoothing of the hair and limit regains in volume to 1.

The disclosed method for shaping the hair may contribute even more care to the hair, without leaving a residual odor on the latter after it has been employed.

It has been found that it may be possible to overcome at least one of the disadvantages of the prior art and to meet the abovementioned objectives by employing a method for the treatment of hair fibers without fixing comprising applying to the hair fibers a reducing composition, comprising at least one reducing agent and at least one cationic polymer, and then heating the hair fibers with a heating device at a temperature at least equal to 50° C., the heating being carried out before or after the optional rinsing of the hair fibers, this method also comprising applying to the hair fibers a care composition comprising at least one aminated silicone.

Thus, disclosed herein is a method for shaping hair fibers comprising:

applying to the hair fibers at least one reducing composition comprising at least one reducing agent and at least one cationic polymer, wherein the weight ratio of the at least one reducing agent to the at least one cationic polymer ranges from 0.1:1 to 10:1, rinsing the hair fibers;

applying to the hair fibers at least one care composition, for example, a leave-in care composition, comprising at least one aminated silicone;

optionally rinsing the hair fibers; and heating the hair fibers, using a heating device at a temperature ranging from 50 to 280° C., the heating being carried out either before or after the optional rinsing of the hair fibers.

In at least one embodiment, the weight ratio of the at least one reducing agent to the at least one cationic polymer ranges from 0.5:1 to 8:1, such as from 1:1 to 5:1.

According to the present disclosure, the expression "method for the treatment of hair fibers without fixing" describes a method for the treatment of hair fibers not employing a fixing stage other than fixing in the air. For example, this expression means that use is not made of fixing by applying to the hair fibers an oxidizing composition comprising hydrogen peroxide at a hydrogen peroxide content of greater than 1% by weight with respect to the total weight of the composition (i.e., 2 Volumes), left in contact with the hair for more than 5 minutes.

According to at least one embodiment of the disclosed method, no oxidizing composition is applied.

According to another embodiment, the disclosed method comprises applying an oxidizing composition with very low concentration of hydrogen peroxide, that is to say comprising hydrogen peroxide at a content of less than 1% by weight with respect to the total weight of the oxidizing composition (i.e., 2 Volumes), and this composition is left to act for a period of time of less than 5 minutes. This oxidizing composition may be useful for neutralizing odors.

Reducing Composition

In at least one embodiment, the at least one reducing composition comprises at least one thiol-comprising reducing agent.

For example, the at least one thiol-comprising reducing agent used as the at least one reducing agent in the at least one reducing composition may be chosen from aminothiols, such as cysteine and its derivatives, for example N-acetylcysteine, cysteamine and its derivatives, such as its $C_1$-$C_4$ acylated derivatives, such as N-acetylcysteamine and N-propionylcysteamine, and non-aminated thiols, such as thiolactic acid and its esters, for example glycerol monothiolactate, thioglycolic acid and its esters, such as glycerol monothioglycolate or glycol monothioglycolate, and thioglycerol.

When the thiol has at least one carboxylic acid functional group it is possible, if appropriate, to use the said thiol in the form of at least one of its salts, such as alkali metal or ammonium salt. Use may thus be made, as thiol, of ammonium thioglycolate. If the thiol has an amino group, it is possible, if appropriate, to use the said thiol in the form of at least one of its salts, such as aminothiol halides. Use may thus be made, as thiol, in the context of the present disclosure, of L-cysteine hydrochloride.

Non-limiting mention may also be made, as aminothiols which can be used in the at least one reducing composition according to the disclosed method, of N-mercaptoalkylamides of sugars, such as N-(2-mercaptoethyl)gluconamide, pantethine, N-(mercaptoalkyl)- or hydroxyalkylamides, such as those described in Patent Application EP-A-354 835, and N-mono- or N,N-dialkylmercapto-4-butyramides, such as those described in Patent Application EP-A-368 763, aminomercaptoalkylamides, such as those described in Patent Application EP-A-432 000, and alkylaminomercaptoalkylamides, such as those described in Patent Application EP-A-514 282. Non-limiting mention may also be made, among the non-aminated thiols that may be used in the method disclosed herein, of the mixture of 2-hydroxypropyl thioglycolate (2/3) and of 2-hydroxy-1-methylethyl thioglycolate (67/33) described in Patent Application FR-A-2 679 448, β-mercaptopropionic acid and its derivatives, and thiomalic acid.

For example, according to the method disclosed herein, use may be made of at least one thiol-comprising reducing agent, such as thioglycolic acid or cysteine.

The at least one reducing agent, for example the at least one thiol, may be present in the at least one reducing composition in an amount ranging from 0.1% to 5%, with respect to the total weight of the at least one reducing composition.

Cationic Polymer

Within the context of the present disclosure, the expression "cationic polymer" denotes any polymer comprising cationic groups and/or groups which can be ionized to give cationic groups.

The at least one cationic polymer which can be used in accordance with the method disclosed herein can be chosen from all of those already known per se as improving the cosmetic properties of the hair, for example those described in Patent Application EP-A-337 354 and in French Patents FR-2 270 846, 2 383 660, 2 598 611, 2 470 596, and 2 519 863.

The at least one cationic polymer may for example be chosen from those which comprise units comprising primary, secondary, tertiary, and/or quaternary amine groups which can either form part of the main polymer chain or are carried by a side substituent directly connected to the main chain.

The at least one cationic polymer used may generally have a number-average molecular weight ranging from 500 to $5 \times 10^6$ and for example ranging from $10^3$ to $3 \times 10^6$.

Non-limiting mention may for example be made, among the cationic polymers, of polymers of the polyamine, polyaminoamide, and polyquaternary ammonium type.

These are known products. They are described for example in French Patents No. 2 505 348 or 2 542 997. Non-limiting mention may be made, among the said polymers of:

(1) Crosslinked or noncrosslinked homopolymers or copolymers derived from acrylic esters, methacrylic esters, acrylamides, or methacrylamides, and comprising at least one of the units chosen from those of the following formulae (I), (II), (III), and (IV):

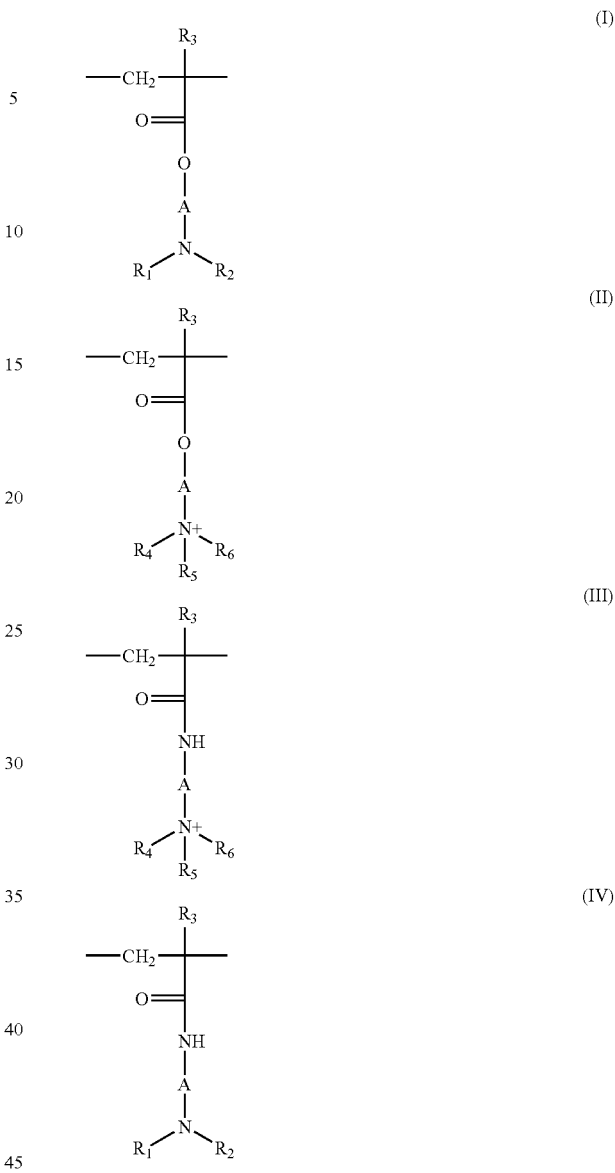

wherein:

$R_3$ denotes a hydrogen atom or a $CH_3$ radical;

A represents a linear or branched alkyl group of 1 to 6 carbon atoms, for example 2 or 3 carbon atoms, or a hydroxyalkyl group of 1 to 4 carbon atoms;

$R_4$, $R_5$ and $R_6$, which are identical or different, represent an alkyl group having from 1 to 6 carbon atoms or a benzyl group, such as an alkyl group having from 1 to 6 carbon atoms;

$R_1$ and $R_2$, which are identical or different, represent hydrogen or an alkyl group having from 1 to 6 carbon atoms, such as methyl or ethyl;

$X^-$ denotes an anion derived from an inorganic or organic acid, such as a methyl sulphate anion or a halide, such as chloride or bromide.

The polymers of the family (1) can further comprise at least one unit deriving from comonomers which can be chosen from the family of the acrylamides, methacrylamides, diacetone acrylamides, acrylamides, and methacrylamides substituted on the nitrogen by lower ($C_1$-$C_4$) alkyls, of the acrylic or methacrylic acids or their esters, of the vinyllactams, such as vinylpyrrolidone or vinylcaprolactam, or of the vinyl esters.

Thus, non-limiting mention may be made, among these polymers of the family (1), of:

copolymers of acrylamide and of dimethylaminoethyl methacrylate which is quaternized with dimethyl sulphate or with a dimethyl halide, such as that sold under the name HERCOFLOC by Hercules, copolymers of acrylamide and of methacryloyloxyethyltrimethylammonium chloride, described, for example, in Patent Application EP-A-080 976 and sold under the name BINA QUAT P 100 by Ciba-Geigy, the copolymer of acrylamide and of methacryloyloxyethyltrimethylammonium methyl sulphate sold under the name RETEN by Hercules, vinylpyrrolidone/dialkylaminoalkyl acrylate or methacrylate copolymers, which may or may not be quaternized, such as the products sold under the name "GAFQUAT" by ISP, like for example "GAFQUAT 734" or "GAFQUAT 755", or the products named "COPOLYMER 845, 958 and 937". These polymers are described in detail in French Patents 2 077 143 and 2 393 573, dimethylaminoethyl methacrylate/vinylcaprolactam/vinylpyrrolidone terpolymers, such as the product sold under the name GAFFIX VC 713 by ISP, vinylpyrrolidone/methacrylamidopropyldimethylamine copolymers, sold for example under the name STYLEZE CC 10 by ISP, quaternized vinylpyrrolidone/dimethylaminopropylmethacrylamide copolymers, such as the product sold under the name "GAFQUAT HS100" by ISP, crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized by methyl chloride or by copolymerization of acrylamide with dimethylaminoethyl methacrylate quaternized by methyl chloride, the homo- or copolymerization being followed by a crosslinking by a compound possessing olefinic unsaturation, such as methylenebisacrylamide. Use may for example be made of a crosslinked acrylamide/methacryloyloxyethyltrimethylammonium chloride (20/80 by weight) copolymer in the form of a dispersion comprising 50% by weight of the said copolymer in mineral oil. This dispersion is sold under the name of "SALCARE® SC 92" by Ciba. Use may also be made of a crosslinked homopolymer of methacryloyloxyethyltrimethylammonium chloride comprising 50% by weight of the homopolymer in mineral oil or in a liquid ester. These dispersions are sold under the names of "SALCARE® SC 95" and "SALCARE® SC 96" by Ciba.

(2) Cationic polysaccharides chosen for example from:

a) The cellulose ether derivatives comprising quaternary ammonium groups described in French Patent 1 492 597 and for example the polymers sold under the "JR" (JR 400, JR 125, JR 30M) or "LR" (LR 400, LR 30M) names by Union Carbide Corporation. These polymers are also defined in the CTFA dictionary as quaternary ammoniums of hydroxyethylcellulose having reacted with an epoxide substituted by a trimethylammonium group.

b) Cellulose copolymers or cellulose derivatives which are grafted with a water-soluble quaternary ammonium monomer, and which are described for example in U.S. Pat. No. 4,131,576, such as hydroxyalkylcelluloses, for example hydroxymethyl-, hydroxyethyl- or hydroxypropylcelluloses, grafted for example with a methacryloyloxyethyltrimethylammonium, methacrylamidopropyltrimethylammonium or dimethyldiallylammonium salt.

The commercially available products corresponding to this definition are for example the products sold under the name "CELQUAT L 200" and "CELQUAT H 100" by National Starch.

c) Guar gums comprising trialkylammonium cationic groups. Use may be made, for example, of guar gums modified by a 2,3-epoxypropyltrimethylammonium salt (for example chloride).

Such products are sold for example under the trade names of JAGUAR C13 S, JAGUAR C 15, JAGUAR C 17, or JAGUAR C162 by Meyhall.

(3) Polymers composed of piperazinyl units and of straight- or branched-chain divalent alkylene or hydroxyalkylene radicals, optionally interrupted by oxygen, sulphur or nitrogen atoms or by aromatic or heterocyclic rings, as well as the oxidation and/or quaternization products of these polymers. Such polymers are described for example in French Patents 2 162 025 and 2 280 361.

(4) Water-soluble polyaminoamides prepared for example by polycondensation of an acidic compound with a polyamine; these polyaminoamides can be crosslinked by an epihalohydrin, a diepoxide, a dianhydride, an unsaturated dianhydride, a bisunsaturated derivative, a bishalohydrin, a bisazetidinium, a bishaloacyldiamine or an alkyl bishalide or alternatively by an oligomer resulting from the reaction of a bifunctional compound reactive with respect to a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mol per amine group of the polyaminoamide; these polyaminoamides can be alkylated or, if they comprise at least one tertiary amine functional group, quaternized. Such polymers are described for example in French Patents 2 252 840 and 2 368 508.

(5) Polyaminoamide derivatives resulting from the condensation of polyalkylenepolyamines with polycarboxylic acids, followed by an alkylation by bifunctional agents. Non-limiting mention may be made, for example, of adipic acid/dialkylaminohydroxyalkyl/dialkylenetriamine polymers in which the alkyl radical comprises from 1 to 4 carbon atoms and for example denotes methyl, ethyl, or propyl. Such polymers are described for instance in French Patent 1 583 363.

Non-limiting mention may also for example be made, among these derivatives, of the adipic acid/dimethylaminohydroxypropyl/diethylenetriamine polymers sold under the name "CARTARETINE F, F4 or F8" by Sandoz.

(6) Polymers obtained by reaction of a polyalkylenepolyamine comprising two primary amine groups and at least one secondary amine group with a dicarboxylic acid chosen from diglycolic acid and saturated aliphatic dicarboxylic acids having from 3 to 6 carbon atoms, the molar ratio of polyalkylenepolyamine to dicarboxylic acid ranging from 0.8:1 to 1.4:1; the polyaminoamide resulting therefrom being brought to react with epichlorohydrin in a molar ratio of epichlorohydrin to the secondary amine group of the polyaminoamide ranging from 0.5:1 to 1.8:1. Such polymers are described for example in U.S. Pat. Nos. 3,227,615 and 2,961,347.

Polymers of this type are for example sold under the name "HERCOSETT 57" by Hercules Inc. or else under the name of "PD 170" or "DELSETTE 101" by Hercules in the case of the adipic acid/epoxypropyl/diethylenetriamine copolymer.

(7) Cyclopolymers of alkyldiallylamine or cyclopolymers of dialkyldiallylammonium, such as the homopolymers and copolymers comprising, as main constituent of the chain, units chosen from those of formulae (V) and (VI):

$$—(CH_2)t—CR_9\underset{H_2C}{\overset{(CH_2)k}{\diagup}}\underset{N^+}{\diagdown}\underset{CH_2}{\overset{C(R_9)—CH_2—}{\diagdown}}\quad Y^- \qquad (V)$$
$$\qquad\qquad\qquad\qquad R_7\ R_8$$

$$—(CH_2)t—CR_9\underset{H_2C}{\overset{(CH_2)k}{\diagup}}\underset{N}{\diagdown}\underset{CH_2}{\overset{C(R_9)—CH_2—}{\diagdown}}\qquad (VI)$$
$$\qquad\qquad\qquad\qquad R_7$$

wherein:

k and t are equal to 0 or 1, the sum k+t being equal to 1;

$R_9$ denotes a hydrogen atom or a methyl radical;

$R_7$ and $R_8$, independently of one another, denote an alkyl group having from 1 to 6 carbon atoms, a hydroxyalkyl group in which the alkyl group for example has from 1 to 5 carbon atoms, or a lower ($C_1$-$C_4$) amidoalkyl group or else $R_7$ and $R_8$ can denote, jointly with the nitrogen atom to which they are attached, heterocyclic groups, such as piperidinyl or morpholinyl; $R_7$ and $R_8$, independently of one another, for example denote an alkyl group having from 1 to 4 carbon atoms;

$Y^-$ is an anion, such as bromide, chloride, acetate, borate, citrate, tartrate, bisulphate, bisulphite, sulphate, or phosphate. These polymers are described for example in French Patent 2 080 759 and in its Certificate of Addition 2 190 406.

Non-limiting mention may for example be made, among the polymers defined above, of the homopolymer of dimethyldiallylammonium chloride sold under the name "MERQUAT 100" by Calgon (and its homologues of low weight-average molecular weight) and of the copolymers of diallyldimethylammonium chloride and of acrylamide sold under the name "MERQUAT 550".

(8) Diquaternary ammonium polymers comprising repeat units corresponding to those of formula (VII):

$$—\underset{\underset{R_{11}\ X^-}{|}}{\overset{\overset{R_{10}}{|}}{N^+}}—A_1—\underset{\underset{R_{13}\ X^-}{|}}{\overset{\overset{R_{12}}{|}}{N^+}}—B_1— \qquad (VII)$$

wherein:

$R_{10}$, $R_{11}$, $R_{12}$, and $R_{13}$, which are identical or different, represent aliphatic, alicyclic or arylaliphatic radicals comprising from 1 to 6 carbon atoms or lower aliphatic hydroxyalkyl radicals or else $R_{10}$, $R_{11}$, $R_{12}$, and $R_{13}$, together or separately, constitute, with the nitrogen atoms to which they are attached, heterocycles optionally comprising a second heteroatom other than nitrogen or else $R_{10}$, $R_{11}$, $R_{12}$, and $R_{13}$ represent a linear or branched $C_1$-$C_6$ alkyl radical substituted by a nitrile, ester, acyl, amide or —CO—O—$R_{14}$-D or —CO—NH—$R_{14}$-D group, where $R_{14}$ is an alkylene and D is a quaternary ammonium group;

$A_1$ and $B_1$ represent polymethylene groups comprising from 2 to 20 carbon atoms which can be linear or branched and saturated or unsaturated, and which can comprise, bonded to or inserted into the main chain, at least one aromatic ring or at least one oxygen or sulphur atom or sulphoxide, sulphone, disulphide, amino, alkylamino, hydroxyl, quaternary ammonium, ureido, amide or ester group, and $X^-$ denotes an anion derived from an inorganic or organic acid;

$A_1$, $R_{10}$, and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group:

$$—(CH_2)_n—CO\text{-}D\text{-}OC—(CH_2)_n—$$

wherein n ranges from 1 to 100, for example from 1 to 50, and D denotes:

a) a glycol residue of formula —O—Z—O—, wherein Z denotes a linear or branched hydrocarbon radical or a group corresponding to one of the following formulae:

$$—(CH_2—CH_2—O)_x—CH_2—CH_2—$$

$$—[CH_2—CH(CH_3)—O]_y—CH_2—CH(CH_3)—$$

wherein x and y denote an integer ranging from 1 to 4, representing a defined and unique degree of polymerization, or any number from 1 to 4 representing a mean degree of polymerization;

b) a bissecondary diamine residue, such as a piperazine derivative;

c) a bisprimary diamine residue of formula —NH—Y—NH—, where Y denotes a linear or branched hydrocarbon radical or else the divalent radical:

$$—CH_2—CH_2—S—S—CH_2—CH_2—;$$

d) a ureylene group of formula —NH—CO—NH—.

For example, $X^-$ is an anion, such as chloride or bromide.

These polymers may have a number-average molecular weight generally ranging from 1,000 to 100,000.

Polymers of this type are described for example in French Patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may for example be made of the polymers which are composed of repeat units corresponding to those of formulae (VIII):

$$—\underset{\underset{R_{11}\ X^-}{|}}{\overset{\overset{R_{10}}{|}}{N^+}}—(CH_2)_n—\underset{\underset{R_{13}\ X^-}{|}}{\overset{\overset{R_{12}}{|}}{N^+}}—(CH_2)_p— \qquad (VIII)$$

wherein $R_{10}$, $R_{11}$, $R_{12}$ and $R_{13}$, which are identical or different, denote an alkyl or hydroxyalkyl radical having from 1 to 4 carbon atoms, n and p are integers ranging from 2 to 20 and $X^-$ is an anion derived from an inorganic or organic acid.

(9) Polyquaternary ammonium polymers composed of units of formula (IX):

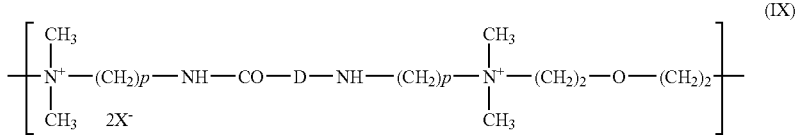

(IX)

wherein:

p denotes an integer ranging from 1 to 6,

D can be nonexistent or can represent a group:

—(CH$_2$)$_r$—CO—, wherein r denotes a number equal to 4 or to 7, and

X$^-$ is an anion derived from an inorganic or organic acid.

Cationic polymers comprising units of formula (IX) are described for example in Patent Application EP-A-122 324 and can be prepared according to the processes described in U.S. Pat. Nos. 4,157,388, 4,390,689, 4,702,906, and 4,719,282.

Among these polymers, non-limiting mention may be made of those with a molecular weight, measured by carbon-13 NMR, of less than 100,000 and in the formula of which:

p is equal to 3, and a) D represents a —(CH$_2$)$_4$—CO— group and X denotes a chlorine atom, the molecular weight, measured by carbon-13 NMR ($^{13}$C NMR) being 5,600; a polymer of this type is provided by Miranol under the name of MIRAPOL-AD1, b) D represents a —(CH$_2$)$_7$—CO— group and X denotes a chlorine atom, the molecular weight, measured by carbon-13 NMR ($^{13}$C NMR) being 8,100; a polymer of this type is provided by Miranol under the name of MIRAPOL-AZ1, c) D denotes the value zero and X denotes a chlorine atom, the molecular weight, measured by carbon-13 NMR ($^{13}$C NMR), being 25,500; a polymer of this type is sold by Miranol under the name MIRAPOL-A15, d) a "block copolymer" formed of units corresponding to the polymers described in paragraphs a) and c), provided by Miranol under the names MIRAPOI-9, ($^{13}$C NMR molecular weight, 7,800) MIRAPOL-175, ($^{13}$C NMR molecular weight, 8,000) and MIRAPOL-95, ($^{13}$C NMR molecular weight, 12,500).

For example, non-limiting mention may be made of the polymer comprising units of formula (XI) in which p is equal to 3, D denotes the value zero and X denotes a chlorine atom, the molecular weight, measured by carbon-13 NMR ($^{13}$C NMR), being 25,500.

(10) Quaternary polymers of vinylpyrrolidone and of vinylimidazole, such as, for example, the products sold under the names LUVIQUAT FC 905, FC 550, and FC 370 by BASF.

(11) Polyamines, such as POLYQUART H, sold by Henkel, which are referenced under the name of "Polyethylene Glycol (15) Tallow Polyamine" in the CTFA dictionary.

Other cationic polymers which can be used in the context of the method disclosed herein are polyalkyleneimines, for example polyethyleneimines, polymers comprising vinylpyridine or vinylpyridinium units, condensates of polyamines and of epichlorohydrin, quaternary polyureylenes and chitin derivatives.

In at least one embodiment, among all the cationic polymers capable of being used in the context of the method disclosed herein, the polymers of the families (7) and (8) are used.

The at least one cationic polymer according to the method disclosed herein is present in an amount ranging from 0.01 to 10% by weight, such as from 0.1 to 5% by weight, with respect to the total weight of the at least one reducing composition.

In at least one embodiment, the at least one cationic polymer is chosen from hexadimethrine chloride and homo- or copolymers of dimethyldiallylammonium chloride.

For example, the pH of the at least one reducing composition ranges from 4 to 12, such as from 7 to 11.

The pH of the at least one reducing composition can be adjusted using an alkaline agent, such as, for example, ammonia, organic amines, such as monoethanolamine, diethanolamine, triethanolamine, 1,3-propanediamine, 2-amino-2-methylpropanol or 2-methyl-1-aminopropanol, an alkali metal or ammonium carbonate or bicarbonate, an organic carbonate, such as guanidine carbonate, or an alkali metal hydroxide, such as sodium hydroxide, or else using an acidifying agent, such as, for example, hydrochloric acid, acetic acid, lactic acid, oxalic acid, or boric acid.

The at least one reducing composition generally comprises at least one cosmetically acceptable solvent chosen for example from water, $C_1$-$C_6$ alcohols, for instance alkanols, such as ethanol, propanol and isopropanol, polyols, such as propylene glycol, pentanediol, glycerol and hexylene glycol, benzyl alcohol, polyol ethers, $C_2$-$C_6$ esters, N-methylpyrrolidone (NMP) and $C_3$-$C_6$ ketones.

With the aim of improving the properties of the hair compositions according to the present disclosure, the at least one reducing composition used according to the method disclosed herein can also comprise at least one cosmetic additive.

The at least one cosmetic additive may generally be chosen from volatile or non-volatile and linear or cyclic silicones, nonionic, anionic or amphoteric polymers, in a soluble or insoluble form, such as latexes, peptides and their derivatives, protein hydrolysates, waxes, swelling and penetrating agents or agents which make it possible to reinforce the effectiveness of the at least one reducing agent, such as the SiO$_2$/polydimethylsiloxane mixture, dimethylisosorbitol, urea and its derivatives, anionic, cationic, nonionic, amphoteric or zwitterionic surface-active agents, agents for combating hair loss, antidandruff agents, natural or synthetic and associative or nonassociative thickeners, suspending agents, sequestering agents, opacifying agents, colorants, sunscreens, vitamins or provitamins, fatty acids, fatty alcohols, mineral, vegetable or synthetic oils, mineral particles, and also fragrances and preservatives, and their mixtures.

In at least one embodiment, the at least one cosmetic additive can be chosen from silicones.

Non-limiting mention may be made, as silicones which can be used as the at least one cosmetic additive in the method disclosed herein, of polydimethylsiloxanes, quaternized polyorganosiloxanes, such as those described in French Patent Application FR 2 535 730, polyorganosiloxanes comprising aminoalkyl groups modified by alkoxycarbonylalkyl groups, such as those described in U.S. Pat. No. 4,749,732, polyorganosiloxanes, such as the polydimethylsiloxane/ polyoxyalkyl copolymer of the dimethicone copolyol type, a polydimethylsiloxane comprising stearoxy end groups (stearoxy dimethicone), a polydimethylsiloxane/dialkylammonium acetate copolymer or a polydimethylsiloxane/poly (alkyl betaine) copolymer which are described in British Patent GB 2 197 352, or polysiloxanes organomodified by mercapto or mercaptoalkyl groups, such as those described in French Patent FR 1 530 369 and in European Patent Application EP 295 780.

Furthermore, the at least one cosmetic additive also can be chosen from fatty acids and fatty alcohols.

Non-limiting mention may for example be made, as fatty acids which can be used as active principles in the method disclosed herein, of $C_8$-$C_{30}$ carboxylic acids, such as palmitic acid, oleic acid, linoleic acid, myristic acid, stearic acid, lauric acid, and their mixtures.

Non-limiting mention may for example be made, as fatty alcohols which can be used in the method disclosed herein, of $C_8$-$C_{30}$ alcohols, such as, for example, palmityl alcohol, oleyl alcohol, linoleyl alcohol, myristyl alcohol, stearyl alcohol, lauryl alcohol, and their mixtures.

The at least one reducing composition used in the method disclosed herein can be provided in the form of a lotion, which is or is not thickened, of a cream, of a gel, or of a foam.

After the application of the at least one reducing composition, the said at least one composition can be left to stand, generally for 5 to 60 minutes, such as for 5 to 30 minutes, optionally under a hood dryer.

Care Composition Comprising at Least One Aminated Silicone

For the purposes of the present disclosure, "silicone" or "polysiloxane" is intended to denote, in conformity with what is generally accepted, any organosilicon polymer or oligomer comprising a branched or crosslinked, linear or cyclic structure of variable molecular weight obtained by polymerization and/or polycondensation of suitably functionalized silanes and essentially composed of a repetition of main units in which the silicon atoms are connected to one another via oxygen atoms (siloxane bond ≡Si—O—Si≡), optionally substituted hydrocarbon radicals being directly bonded via a carbon atom to the said silicon atoms. The commonest hydrocarbon radicals are alkyl radicals, for example $C_1$-$C_{10}$ alkyl radicals such as methyl radicals, fluoroalkyl radicals, aryl radicals and for instance phenyl radicals, and alkenyl radicals and for instance vinyl radicals; other types of radicals capable of being bonded either directly or via a hydrocarbon radical to the siloxane chain are for example hydrogen, halogens such as chlorine, bromine or fluorine, thiols, alkoxy radicals, polyoxyalkylene (or polyether) radicals and for example polyoxyethylene and/or polyoxypropylene radicals, hydroxyl or hydroxyalkyl radicals, amide groups, acyloxy or acyloxyalkyl radicals, amphoteric or betaine groups, or anionic groups, such as carboxylate, thioglycolate, sulphosuccinate, thiosulphate, phosphate, and sulphate groups, this list, of course, being in no way limiting ("organomodified" silicones).

According to the present disclosure, the at least one aminated silicone is any silicone comprising at least one group chosen from primary, secondary, and tertiary amine groups and quaternary ammonium group. Non-limiting mention may thus be made of:

(a) the polysiloxanes of formula (X):

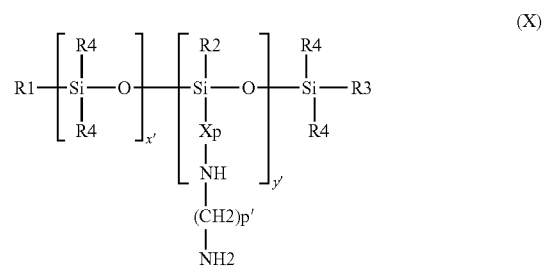

wherein x' and y' are integers dependent on the molecular weight, generally such that the said weight-average molecular weight ranges from 5,000 to 500,000;

R1, R2, and R3, which are identical or different, denote a hydroxyl radical, a $C_1$ to $C_4$ alkyl radical, a $C_1$ to $C_4$ alkoxy radical, or a phenyl radical;

X denotes a branched or unbranched $C_1$-$C_4$ alkylene radical;

R4 denotes a $C_1$-$C_4$ alkyl radical or a phenyl radical;

p and p' denote, independently of one another, an integer ranging from 1 to 10.

In at least one embodiment, alkyl denotes methyl and alkoxy denotes methoxy.

In at least one embodiment, p=3, p'=2, R4 denotes methyl and X denotes methylene.

Non-limiting mention may be made, among these polymers, of the compounds denoted by the names "amodimethicone" and "trimethylsilylaminodimethicone" in the CTFA dictionary.

(b) the aminated silicones of formula (XI):

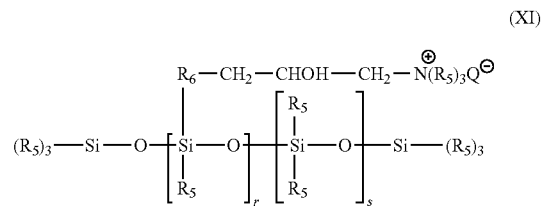

wherein:

$R_5$ represents a monovalent hydrocarbon radical having from 1 to 18 carbon atoms such as a $C_1$-$C_{18}$ alkyl or $C_2$-$C_{18}$ alkenyl radical, for example a methyl radical;

$R_6$ represents a divalent hydrocarbon radical, such as a $C_1$-$C_{18}$ alkylene radical or a divalent $C_1$-$C_{18}$ alkyleneoxy radical, for example having from 1 to 8 carbon atoms, connected to the Si via an SiC bond;

$Q^-$ is an anion, such as a halide ion, such as a chloride ion, or an organic acid salt (acetate, and the like);

r represents a mean statistical value ranging from 2 to 20 such as from 2 to 8;

s represents a mean statistical value ranging from 20 to 200 such as from 20 to 50.

Such aminated silicones are described for example in U.S. Pat. No. 4,185,087.

A silicone coming within this category is the silicone sold by Union Carbide under the name "UCAR SILICONE ALE 56".

(c) the quaternary ammonium silicones of formula (XIb):

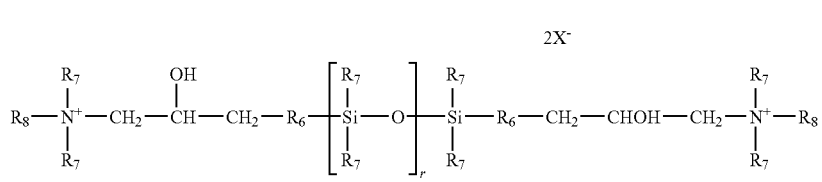

(XIb)

wherein:

R_7, which are identical or different, represent a monovalent hydrocarbon radical having from 1 to 18 carbon atoms, such as a $C_1$-$C_{18}$ alkyl radical or a $C_2$-$C_{18}$ alkenyl radical, or a ring comprising 5 or 6 carbon atoms, for example methyl;

R_6 represents a divalent hydrocarbon radical, such as a $C_1$-$C_{18}$ alkylene radical or a divalent $C_1$-$C_{18}$ alkyleneoxy radical, for example having from 1 to 8 carbon atoms, connected to the Si via an SiC bond;

R_8, which are identical or different, represent a hydrogen atom, a monovalent hydrocarbon radical having from 1 to 18 carbon atoms, such as a $C_1$-$C_{18}$ alkyl radical or a $C_2$-$C_{18}$ alkenyl radical, or an —R_6—NHCOR_7 radical;

X⁻ is an anion, such as a halide ion, for example a chloride ion, or an organic acid salt (acetate, and the like);

r represents a mean statistical value ranging from 2 to 200 such as from 5 to 100.

These silicones are, for example, described in Application EP-A-0530974.

According to the method disclosed herein, use may be made for example of an aminated silicone:

the amine number of which is greater than 0.15 meq per gram, having hydroxyl and/or alkoxy ends.

Non-limiting mention may be made, by way of example, as microemulsion comprising such a silicone, of the product sold by Wacker under the name of WACKER-BELSIL ADM LOG 1.

The aminated silicones can be provided in the microemulsion form.

In at least one embodiment, the at least one aminated silicone is present in a pretreatment or post-treatment care composition in an amount ranging from 0.05 to 10% by weight, with respect to the total weight of the composition, such as ranging from 0.1 to 7%.

The at least one care composition comprising at least one aminated silicone can comprise water-soluble or fat-soluble active principles having a cosmetic activity. Non-limiting mention may be made, as examples of active principle, of vitamins and their derivatives, such as vitamin E, vitamin E acetate, vitamin C and its esters, vitamins B, vitamin A alcohol or retinol, or vitamin A acid or retinoic acid and its derivatives, provitamins, such as panthenol, vitamin A palmitate, niacinamide, ergocalciferol, antioxidants, essential oils, humectants, silicone or non-silicone sunscreens, preservatives, sequestering agents, pearlescent agents, pigments, moisturising agents, antidandruff agents, antiseborrheic agents, plasticizers, hydroxy acids, electrolytes, and fragrances. The at least one care composition comprising at least one aminated silicone can comprise at least one of the additives listed for the at least one reducing composition.

In at least one embodiment, the pH of the at least one care composition comprising at least one aminated silicone ranges from 2 to 10, such as from 3 to 9.

Such care compositions are for example described in EP 1 247 518.

Heating the Fibers

As explained above, the method disclosed herein comprises heating the hair fibers using a heating device.

Use may be made, as a heating device, of a hood dryer, a hairdryer, an iron, with or without addition of steam, for example as described in FR 2 921 805, or an infrared device.

The heating can be preceded by predrying the hair fibers, using at least one heating device.

Within the context of the present disclosure, "iron" is understood to mean a device for heating hair fibers by contact.

The end of the iron coming into contact with the hair fibers can have different forms. It can for example exhibit a flat surface; in this case, the term "flat iron" is used. It can also exhibit a rounded surface; in this case, the term "round iron" is used.

The iron can be applied by successive separate touches of a few seconds or by gradually moving or sliding along the locks.

Non-limiting mention may be made, as examples of iron which can be used in the method disclosed herein, of any type of flat or round iron and for example, without limitation, of those described in U.S. Pat. Nos. 4,103,145, 4,308,878, 5,983,903, 5,957,140, 5,494,058, and 5,046,516.

In at least one embodiment, the hair fibers are heated with a heating device at a temperature ranging from 50° C. to 280° C., such as from 80° C. to 220° C.

In the case of the use of a hood dryer or of a hairdryer, the drying time can range from 1 to 90 minutes.

According to the method disclosed herein, the order of applying to the hair fibers the at least one reducing composition; rinsing the hair fibers; applying to the hair fibers the at least one care composition comprising at least one aminated silicone; optionally rinsing the hair fibers; and heating the hair fibers can be varied. For example, the method disclosed herein can be illustrated by the following non-limiting alternative forms:

Alternative form 1: applying to the hair fibers at least one reducing composition; rinsing the hair fibers; then applying to the hair fibers at least one care composition comprising at least one aminated silicone; optionally rinsing the hair fibers; and then heating the hair fibers with a heating device.

Alternative form 2: applying to the hair fibers at least one care composition comprising at least one aminated silicone; optionally rinsing the hair fibers; then applying to the hair fibers at least one reducing composition; rinsing the hair fibers; and then heating the hair fibers with a heating device.

Alternative form 3: applying to the hair fibers at least one care composition comprising at least one aminated silicone; optionally rinsing the hair fibers, then applying to the hair fibers at least one reducing composition; rinsing the hair fibers; then applying to the hair fibers the at least one care composition comprising at least one aminated silicone; optionally rinsing the hair fibers and then heating the hair fibers with a heating device.

The application to the hair fibers of at least one care composition comprising at least one aminated silicone can optionally be followed by a rinsing operation or by a shampooing operation; in at least one embodiment, the at least one care composition is left on the hair fibers. If the application of the at least one care composition comprising at least one aminated silicone is followed by rinsing, the leave-in time before rinsing ranges from 30 seconds to 10 minutes.

Optional Additional Stages
Application of at Least one Second Care Composition

The method disclosed herein can further comprise applying to the hair fibers at least one second care composition different from the at least one care composition comprising at least one aminated silicone. This at least one second care composition comprises at least one silicone or non-silicone fatty substance.

The at least one fatty substance which can be used in the at least one second care composition according to the method disclosed herein can be chosen from all natural or synthetic, organic or inorganic, and silicone or non-silicone resins, waxes, and oils.

An oil, within the context of the present disclosure, is a lipophilic compound which is liquid at ambient temperature (25° C.) and which exhibits a reversible solid/liquid change in state. Animal and vegetable oils comprise, as essential constituents, triesters of propane-1,2,3-triol.

A wax, within the context of the present disclosure, is a lipophilic compound which is solid at ambient temperature (25° C.), which exhibits a reversible solid/liquid change in state, which has a melting point of greater than 40° C. and which can range up to 200° C., and which exhibits, in the solid state, an anisotropic crystalline arrangement.

Non-Silicone Fatty Substances

Non-limiting mention may be made, as oils which can be used in the at least one second care composition, for example, of:

hydrocarbon oils of animal origin, such as perhydrosqualene;

hydrocarbon oils of vegetable origin, such as liquid triglycerides of fatty acids comprising from 4 to 10 carbon atoms, such as triglycerides of heptanoic or octanoic acids, or also, for example, sunflower, maize, soybean, cucumber, grape seed, sesame, hazelnut, apricot, macadamia, arara, castor or avocado oils, triglycerides of caprylic/capric acids, such as, for example, those sold by Stéarineries Dubois or those sold under the names MIGLYOL 810, 812 and 818 by Dynamit Nobel, jojoba oil or shea butter oil;

synthetic esters and ethers, for example fatty acids, such as oils of formulae $R^6COOR^7$ and $R^6OR^7$ in which $R^6$ represents the residue of a fatty acid comprising from 8 to 29 carbon atoms and $R^7$ represents a branched or unbranched hydrocarbon chain comprising from 3 to 30 carbon atoms, such as, for example, Purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as liquid paraffins, which may or may not be volatile, and their derivatives, petrolatum, polydecenes or hydrogenated polyisobutene, such as parleam oil;

fluid fatty alcohols having from 8 to 26 carbon atoms, such as octyldodecanol, 2-butyloctanol, oleyl alcohol, linoleyl alcohol or linolenyl alcohol;

alkoxylated and for example ethoxylated fatty alcohols, such as oleth-12;

fluorinated oils which partially comprise hydrocarbon, such as those described in the document JP-A-2 295912. Non-limiting mention may also be made, as fluorinated oils, of perfluoromethylcyclopentane and perfluoro-1,3-dimethylcyclohexane, for example sold under the names of "FLUTEC PC1®" and "FLUTEC PC3®" by BNFL Fluorochemicals; perfluoro-1,2-dimethylcyclobutane; perfluoroalkanes, such as dodecafluoropentane and tetradecafluorohexane, for example sold under the names of "PF 5050®" and "PF 5060®" by 3M, or also bromoperfluorooctyl, for example sold under the name "FORALKYL®" by Atochem; nonafluoromethoxybutane, for example sold under the name "MSX 45180" by 3M, and nonafluoroethoxyisobutane; or perfluoromorpholine derivatives, such as 4-(trifluoromethyl) perfluoromorpholine, for example sold under the name "PF 50520" by 3M.

The term "hydrocarbon oil" in the list of the oils mentioned herein is understood to mean any oil comprising predominantly carbon and hydrogen atoms and optionally ester, ether, fluorinated, carboxylic acid and/or alcohol groups.

Animal and vegetable waxes comprise, as essential constituents, esters of carboxylic acids and of alcohols having long chains. Generally, the size of the crystals of the wax is such that the crystals diffract and/or scatter light, conferring a more or less opaque cloudy appearance on the composition comprising them. By bringing the wax to its melting point, it is possible to render it miscible with oils and to form a microscopically homogeneous mixture but, on returning the temperature of the mixture to ambient temperature, recrystallization of the wax in the oils of the mixture, detectable microscopically and macroscopically (opalescence), is obtained.

Non-limiting mention may be made, as waxes which can be used in the method disclosed herein, of waxes of animal origin, such as beeswax, spermaceti, lanolin wax and lanolin derivatives; vegetable waxes, such as sunflower, rice or apple waxes, carnauba, candelilla, ouricury or Japan wax, cocoa butter or cork fiber or sugarcane waxes; mineral waxes, for example paraffin wax, petrolatum wax, lignite wax, microcrystalline waxes, ceresin or ozokerite; synthetic waxes, such as polyethylene waxes or Fischer-Tropsch waxes, and their mixtures.

Silicone Fatty Substances

Use may also be made, in the at least one second care composition disclosed herein, of a silicone as the at least one fatty substance.

The silicones which can be used in the at least one second care composition can be linear, cyclic, branched or unbranched and volatile or nonvolatile. They can be provided in the form of oils, resins, or gums. They can for example be polyorganosiloxanes which are insoluble in the cosmetically acceptable medium.

Organopolysiloxanes are defined in more detail in the work by Walter Noll, "Chemistry and Technology of Silicones" (1968), Academic Press. They can be volatile or nonvolatile.

When they are volatile, the silicones are chosen for example from those having a boiling point ranging from 60° C. to 260° C., and for example from:

(i) cyclic silicones comprising from 3 to 7 silicon atoms such as from 4 to 5. They are, for example, octamethylcyclotetrasiloxane, sold for instance under the name of "VOLATILE SILICONE 7207" by Union Carbide or "SILBIONE 70045 V 2" by Rhodia, decamethylcyclopentasiloxane, sold under the name of "VOLATILE SILICONE 7158" by Union Carbide or "SILBIONE 70045 V 5" by Rhodia, and their mixtures.

Non-limiting mention may also be made of cyclocopolymers of the dimethylsiloxane/methylalkylsiloxane type, such as "SILICONE VOLATILE FZ 3109", sold by Union Carbide, with the chemical structure:

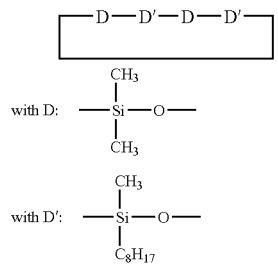

Non-limiting mention may also be made of mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

(ii) linear volatile silicones having 2 to 9 silicon atoms and having a viscosity of less than or equal to $5 \times 10^{-6}$ m$^2$/s at 25° C. They are, for example, decamethyltetrasiloxane, sold for instance under the name "SH 200" by Toray Silicone. Silicones coming within this category are also described in the article published in Cosmetics and Toiletries, Vol. 91, January 76, p. 27-32, Todd & Byers, "Volatile Silicone Fluids for Cosmetics".

Non-limiting mention may for example be made, among nonvolatile silicones, of polyalkylsiloxanes, polyarylsiloxanes, polyalkylarylsiloxanes, silicone gums and resins, polyorganosiloxanes modified by organofunctional groups, and their mixtures.

The organomodified silicones which can be used in accordance with the method disclosed herein are silicones as defined above comprising, in their structure, at least one organofunctional groups attached via a hydrocarbon group.

Non-limiting mention may be made, among organomodified silicones, of polyorganosiloxanes comprising:

polyethyleneoxy and/or polypropyleneoxy groups optionally comprising $C_6$-$C_{24}$ alkyl groups, such as the products named dimethicone copolyol sold by Dow Corning under the name DC 1248 or the oils SILWET® L 722, L 7500, L 77 or L 711 from Union Carbide and the ($C_{12}$)alkyl methicone copolyol sold by Dow Corning under the name Q2 5200;

thiol groups, such as the products sold under the names "GP 72 A" and "GP 71" from Genesee;

alkoxylated groups, such as the product sold under the name "SILICONE COPOLYMER F-755" by SWS Silicones and ABIL WAX® 2428, 2434 and 2440 by Goldschmidt;

hydroxylated groups, such as the polyorganosiloxanes comprising a hydroxyalkyl functional group described in French Patent Application FR-A-85 16334;

acyloxyalkyl groups, such as, for example, the polyorganosiloxanes described in U.S. Pat. No. 4,957,732;

anionic groups of the carboxylic acid type, such as, for example, in the products described in Patent EP 186 507 from Chisso Corporation, or of the alkylcarboxyl type, such as those present in the product X-22-3701E from Shin-Etsu; 2-hydroxyalkylsulphonate type; or 2-hydroxyalkyl thiosulphate type, such as the products sold by Goldschmidt under the names "ABIL® S201" and "ABIL® S255".

The silicone oils which can be used in the at least one second care composition according to the method disclosed herein are volatile or nonvolatile polymethylsiloxanes comprising a linear or cyclic silicone chain which are liquid or pasty at ambient temperature, for example cyclopolydimethylsiloxanes (cyclomethicones), such as cyclohexasiloxane; polydimethylsiloxanes comprising pendent alkyl, alkoxy or phenyl groups or alkyl, alkoxy or phenyl groups at the end of the silicone chain, which groups have from 2 to 24 carbon atoms; phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, (2-phenylethyl)trimethylsiloxysilicates or polymethyl-phenylsiloxanes; and their mixtures.

The silicone gums which can be used in the at least one second care composition according to the method disclosed herein are polydiorganosiloxanes of high molecular weight, ranging from 200,000 to 2,000,000, used alone or as a mixture in a solvent chosen from volatile silicones, polydimethylsiloxane oils, polymethylphenylsiloxane oils, polydiphenyldimethylsiloxane oils, isoparaffins, methylene chloride, pentane, hydrocarbons, and their mixtures.

Use may for example be made of a silicone gum with a molecular weight of less than 1,500,000. The silicone gums are, for example, polydimethylsiloxanes, polyphenylmethylsiloxanes, poly(diphenylsiloxane/dimethylsiloxane)s, poly(dimethyl-siloxane/methylvinylsiloxane)s, poly(dimethylsiloxane/phenylmethylsiloxane)s or poly(diphenylsiloxane/dimethylsiloxane/methylvinylsiloxane)s.

These silicone gums can be terminated at the chain end by trimethylsilyl or dimethylhydroxysilyl groups.

The silicone resins which can be used in the at least one second care composition according to the method disclosed herein are crosslinked siloxane systems including the units $R_2SiO_{2/2}$, $RSiO_{3/2}$ and $SiO_{4/2}$ in which R represents a hydrocarbon group having from 1 to 6 carbon atoms or a phenyl group. Those which may for example be used among these products are those in which R denotes a lower ($C_1$-$C_6$) alkyl radical or a phenyl radical.

The at least one silicone or non-silicone fatty substance can be present in the at least one optional second care composition according to the method disclosed herein in an amount ranging from 0.01 to 20% by weight, such as from 0.05 to 10% by weight, with respect to the total weight of the at least one second care composition.

The at least one second care composition can comprise all the additional ingredients disclosed herein for the at least one care composition comprising at least one aminated silicone.

In at least one embodiment, the method disclosed herein comprises applying to the hair fibers the at least one second care composition before applying the at least one reducing composition, and optionally rinsing it out. If it is rinsed out, its leave-in time ranges from 30 seconds to 10 minutes.

The following examples, without, however, being limiting in nature, illustrate the method disclosed herein. The contents are shown as active material.

EXAMPLES

The method for the treatment of hair fiberes disclosed herein was carried out using at least one reducing composition and at least one care composition.

| Reducing composition B | |
|---|---|
| Cysteine | 4 g |
| Hydroxypropyl guar | 0.5 g |
| Mexomere PO | 2.5 g |
| Monoethanolamine | q.s. for pH 9.2 |
| Water | q.s. for 100 g |

| Care composition D | |
|---|---|
| Cetearyl alcohol | 1.5 g |
| Steareth-20 | 0.5 g |
| Wacker-Belsil ADM LOG 1 | 13.5 g |
| Water | q.s. for 100 g |

The method for the treatment of hair fibers disclosed herein was carried out using either a hairdryer or an iron to heat the hair fibers.

1) Example of Method with Hairdryer

In general, this method may be fast and involve little in the way of technique, which allows the user to apply it herself.

The hair (moderately wavy natural hairs) was washed using a standard shampoo and then superficially dried.

The care composition D was applied immediately to the ends, without rinsing, at ambient temperature (22° C.).

The reducing composition B was applied subsequently to the whole of the hair, by hand and using a brush. A leave-in time of 20 min, at ambient temperature, was observed and then the hair was rinsed copiously with water.

The care composition D was applied to the whole of the hair, and the hair was predried with a hairdryer. Careful blow drying was subsequently carried out on the whole of the hair, still with a hairdryer and a brush, at a temperature of 60° C.

At the end, the hair was smooth and without frizziness and the fibers were easy to style and to disentangle. The hairs were not damaged.

In the days following, and up to 8 shampooings, the hairs remained easy to style, with less in the way of frizziness or slackened curls. Blow drying was rapid and easy.

2) Example of Method with Iron

In general, this method may be more technical than the preceding one but it may exhibit a smoother and more persistent result, while being reversible.

The hair (moderately wavy natural hairs) was washed using a standard shampoo and then superficially dried.

The care composition D was applied immediately to the ends, without rinsing, at ambient temperature (22° C.).

The reducing composition B was applied subsequently to the whole of the hair, by hand and using a brush. A leave-in time of 20 min, at ambient temperature, was observed, and then the hair was rinsed copiously with water.

The care composition D was applied to the whole of the hair and the hair was predried with a hairdryer. Careful smoothing was subsequently carried out on the whole of the hair with a flat iron, the temperature of which was 180° C.

The hair was smooth and without frizziness and the fibers were easy to style and to disentangle.

In the days following, and up to 10 shampooings, the hairs remained easy to style, with less in the way of frizziness and slack curls. Daily blow drying was rapid and easy.

The hairs were not damaged and the residual odor was faint.

What is claimed is:

1. A method for shaping hair fibers comprising:
    applying to the hair fibers at least one reducing composition comprising at least one reducing agent and at least one cationic polymer, wherein the weight ratio of the at least one reducing agent to the at least one cationic polymer ranges from 0.1:1 to 10:1,
    rinsing the hair fibers;
    applying to the hair fibers at least one care composition comprising at least one aminated silicone;
    optionally rinsing the hair fibers; and
    heating the hair fibers with a heating device at a temperature ranging from 50 to 280° C., the heating being carried out either before or after the optional rinsing of the hair fibers;
    wherein the reducing composition does not comprise ammonium bicarbonate; and further wherein an oxidizing composition is not applied to the hair fibers.

2. The method according to claim 1, wherein the weight ratio of the at least one reducing agent to the at least one cationic polymer ranges from 0.5:1 to 8:1.

3. The method according to claim 2, wherein the weight ratio of the at least one reducing agent to the at least one cationic polymer ranges from 1:1 to 5:1.

4. The method according to claim 1, wherein the at least one cationic polymer is chosen from cyclopolymers of alkyldiallylamine and cyclopolymers of dialkyldiallylammonium.

5. The method according to claim 1 wherein the at least one cationic polymer is chosen from diquaternary ammonium polymers comprising repeat units corresponding to those of formula (VII):

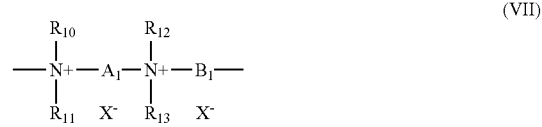

(VII)

wherein:
  $R_{10}$, $R_{11}$, $R_{12}$, and $R_{13}$, which are identical or different, represent aliphatic, alicyclic or arylaliphatic radicals comprising from 1 to 6 carbon atoms or lower aliphatic hydroxyalkyl radicals or else $R_{10}$, $R_{11}$, $R_{12}$, and $R_{13}$, together or separately, constitute, with the nitrogen atoms to which they are attached, heterocycles optionally comprising a second heteroatom other than nitrogen or else $R_{10}$, $R_{11}$, $R_{12}$, and $R_{13}$ represent a linear or branched $C_1$-$C_6$ alkyl radical substituted by a nitrile, ester, acyl, amide or —CO—O—$R_{14}$-D or —CO—NH—$R_{14}$-D group, where $R_{14}$ is an alkylene and D is a quaternary ammonium group;
  $A_1$ and $B_1$ represent polymethylene groups comprising from 2 to 20 carbon atoms which can be linear or branched and saturated or unsaturated, and which can comprise, bonded to or inserted into the main chain, at least one aromatic ring or at least one oxygen or sulphur atom or sulphoxide, sulphone, disulphide, amino, alkylamino, hydroxyl, quaternary ammonium, ureido, amide or ester group, and
  $X^-$ denotes an anion derived from an inorganic or organic acid;
  $A_1$, $R_{10}$, and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group:

—$(CH_2)_n$—CO-D-OC—$(CH_2)_n$— wherein n ranges from 1 to 100 and D denotes:
a) a glycol residue of formula —O—Z—O—, where Z denotes a linear or branched hydrocarbon radical or a group corresponding to one of the following formulae:

—$(CH_2$—$CH_2$—$O)_x$—$CH_2$—$CH_2$—

$[CH_2$—$CH(CH_3)$—$O]_y$—$CH_2$—$CH(CH_3)$— where x and y denote an integer from 1 to 4, representing a defined and unique degree of polymerization, or any number from 1 to 4 representing a mean degree of polymerization;
b) a bissecondary diamine residue;
c) a bisprimary diamine residue of formula —NH—Y—NH— where Y denotes a linear or branched hydrocarbon radical or else the divalent radical

—$CH_2$—$CH_2$—S—S—$CH_2$—$CH_2$—;

d) a ureylene group of formula —NH—CO—NH—.

6. The method according to claim 5, wherein n ranges from 1 to 50.

7. The method according to claim 5, wherein D denotes a piperazine derivative.

8. The method according to claim 1, wherein the at least one reducing agent is present in the at least one reducing composition in an amount ranging from 0.1% to 5%, relative to the total weight of the at least one reducing composition.

9. The method according to claim 1, wherein the at least one cationic polymer is present in the at least one reducing composition in an amount ranging from 0.01 to 10% by weight, relative to the total weight of the at least one reducing composition.

10. The method according to claim 9, wherein the at least one cationic polymer is present in the at least one reducing composition in an amount ranging from 0.1 to 5% by weight, relative to the total weight of the at least one reducing composition.

11. The method according to claim 1, wherein the hair fibers are heated at a temperature ranging from 80° C. to 220° C.

12. The method according to claim 1, wherein the at least one reducing agent is a thiol-comprising reducing agent.

13. The method according to claim 1, wherein the at least one animated silicone is an aminated silicone chosen from those of formula (X):

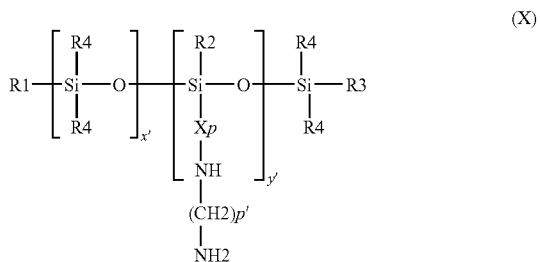

wherein x' and y' are integers dependent on the molecular weight, generally such that the weight-average molecular weight ranges from 5,000 to 500,000;

R1, R2, and R3, which are identical or different, denote a hydroxyl radical, a $C_1$ to $C_4$ alkyl radical, a $C_1$ to $C_4$ alkoxy radical, or a phenyl radical;

X denotes a branched or unbranched $C_1$-$C_4$ alkylene radical;

R4 denotes a $C_1$-$C_4$ alkyl radical or a phenyl radical; and p and p' denote, independently of one another, an integer ranging from 1 to 10.

14. The method according to claim 1, further comprising applying to the hair fibers at least one second care composition different from the at least one care composition comprising at least one aminated silicone, the at least one second care composition comprising at least one silicone or non-silicone fatty substance.

* * * * *